United States Patent
Rohl et al.

(10) Patent No.: US 11,172,921 B2
(45) Date of Patent: Nov. 16, 2021

(54) HEART TISSUE ANCHORS

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: James P. Rohl, Prescott, WI (US); Mary M. Byron, Roseville, MN (US); David R. Wulfman, Minneapolis, MN (US); James K. Cawthra, Jr., Ramsey, MN (US); Devon N. Arnholt, Shoreview, MN (US); Michael Eppihimer, Franklin, MA (US); David J. Lehse, Oakdale, MN (US); Katherine Lorraine Baldwin, Minneapolis, MN (US); Joseph A. Dearani, Rochester, MN (US); Peter M. Pollak, Atlantic Beach, FL (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 298 days.

(21) Appl. No.: 16/313,441

(22) PCT Filed: Dec. 16, 2016

(86) PCT No.: PCT/US2016/067275
§ 371 (c)(1),
(2) Date: Dec. 26, 2018

(87) PCT Pub. No.: WO2017/106713
PCT Pub. Date: Jun. 22, 2017

(65) Prior Publication Data
US 2019/0183481 A1 Jun. 20, 2019

Related U.S. Application Data

(60) Provisional application No. 62/269,451, filed on Dec. 18, 2015.

(51) Int. Cl.
*A61B 17/04* (2006.01)
*A61F 2/24* (2006.01)
(Continued)

(52) U.S. Cl.
CPC ...... *A61B 17/0401* (2013.01); *A61B 17/1227* (2013.01); *A61F 2/2487* (2013.01);
(Continued)

(58) Field of Classification Search
CPC ............ A61B 17/0057; A61B 17/0401; A61B 2017/00247; A61B 2017/00592;
(Continued)

(56) References Cited

U.S. PATENT DOCUMENTS

2004/0122456 A1* 6/2004 Saadat ............. A61B 17/00234
606/157
2005/0148925 A1 7/2005 Rottenberg et al.
(Continued)

FOREIGN PATENT DOCUMENTS

EP 2478868 A1 7/2012
WO 2007083288 A2 7/2007
(Continued)

OTHER PUBLICATIONS

International Search Report and Written Opinion dated Apr. 4, 2017 for International Application No. PCT/US2016/067275.
(Continued)

*Primary Examiner* — Robert A Lynch
(74) *Attorney, Agent, or Firm* — Seager, Tufte & Wickhem, LLP

(57) ABSTRACT

A heart valve anchor has a body that includes a distal portion, a distal end, a proximal portion, and a proximal end. The distal end and the proximal end define a longitudinal axis. The body has an expandable portion that includes a first radially expandable portion at the distal portion of the body,
(Continued)

a second radially expandable portion at the proximal portion of the body, and a root portion disposed between the first and second radially expandable portions. The body has a first configuration adapted to be housed at least partially within a tissue penetrating device, and a second configuration in which the first and second radially expandable portions are partially or fully expanded such that the anchor engages tissue in a region between the first and second radially expandable portions.

10 Claims, 15 Drawing Sheets

(51) Int. Cl.
*A61B 17/122* (2006.01)
*A61B 17/00* (2006.01)
*A61B 17/128* (2006.01)

(52) U.S. Cl.
CPC . *A61B 17/1285* (2013.01); *A61B 2017/00247* (2013.01); *A61B 2017/00592* (2013.01); *A61B 2017/00606* (2013.01); *A61B 2017/00623* (2013.01); *A61B 2017/00783* (2013.01); *A61B 2017/00867* (2013.01); *A61B 2017/0406* (2013.01); *A61B 2017/0409* (2013.01); *A61B 2017/0419* (2013.01); *A61B 2017/0464* (2013.01); *A61F 2230/001* (2013.01); *A61F 2230/0071* (2013.01)

(58) Field of Classification Search
CPC ........... A61B 2017/00606; A61B 2017/00619; A61B 2017/00623; A61B 2017/00654; A61B 2017/0409; A61B 2017/0412; A61B 2017/0414; A61B 2017/0464; A61F 2/2487; A61F 2230/001; A61F 2230/0071
See application file for complete search history.

(56) References Cited

U.S. PATENT DOCUMENTS

| | | |
|---|---|---|
| 2006/0136043 A1 | 6/2006 | Cully et al. |
| 2006/0241690 A1* | 10/2006 | Amplatz ........... A61B 17/12122 606/213 |
| 2007/0066863 A1 | 3/2007 | Rafiee et al. |
| 2007/0112380 A1* | 5/2007 | Figulla ............. A61B 17/12022 606/213 |
| 2007/0112425 A1* | 5/2007 | Schaller ............ A61B 17/0401 623/2.37 |
| 2007/0185572 A1* | 8/2007 | Solem .................. A61F 2/2451 623/2.37 |
| 2008/0009888 A1* | 1/2008 | Ewers ................ A61B 17/0487 606/151 |
| 2008/0249562 A1* | 10/2008 | Cahill ................ A61B 17/0057 606/215 |
| 2008/0249563 A1 | 10/2008 | Cahill |
| 2009/0275974 A1* | 11/2009 | Marchand ........ A61B 17/12113 606/194 |
| 2009/0281557 A1* | 11/2009 | Sander .................. A61B 17/11 606/151 |
| 2012/0053686 A1 | 3/2012 | McNamara et al. |
| 2013/0190798 A1* | 7/2013 | Kapadia ................ A61F 2/2466 606/195 |
| 2014/0012368 A1 | 1/2014 | Sugimoto et al. |
| 2015/0223801 A1* | 8/2015 | Ogdahl ............. A61B 17/0401 600/37 |

FOREIGN PATENT DOCUMENTS

| | | |
|---|---|---|
| WO | 2008055301 A1 | 5/2008 |
| WO | 2012085913 A2 | 6/2012 |
| WO | 2013016618 A2 | 1/2013 |
| WO | 2013036742 A1 | 3/2013 |
| WO | 2016183485 A1 | 11/2016 |

OTHER PUBLICATIONS

International Preliminary Report on Patentability dated Jun. 28, 2018 for International Application No. PCT/US2016/067275.

* cited by examiner

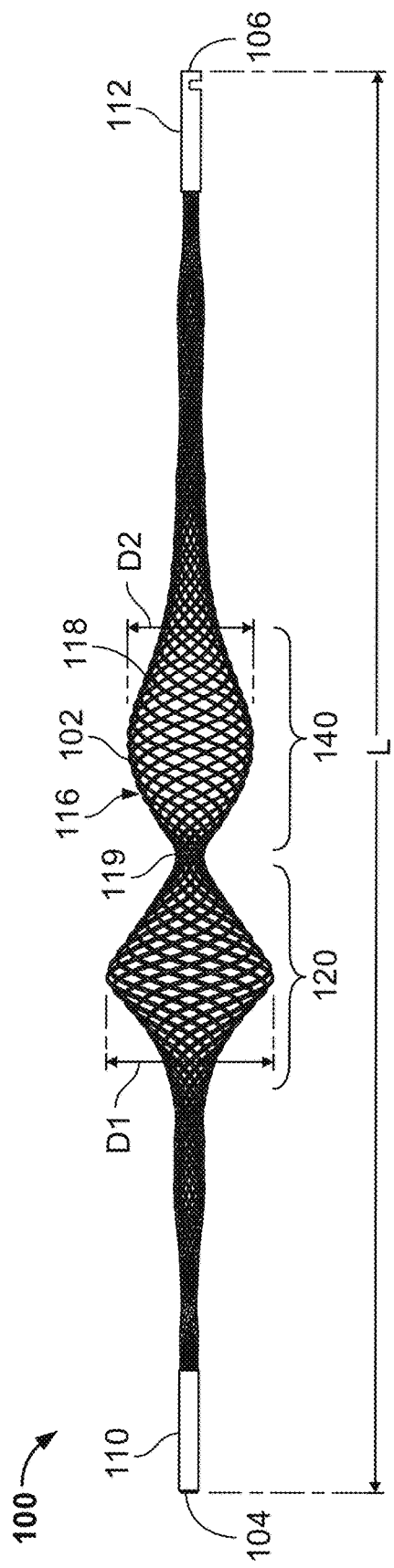
FIG. 3A
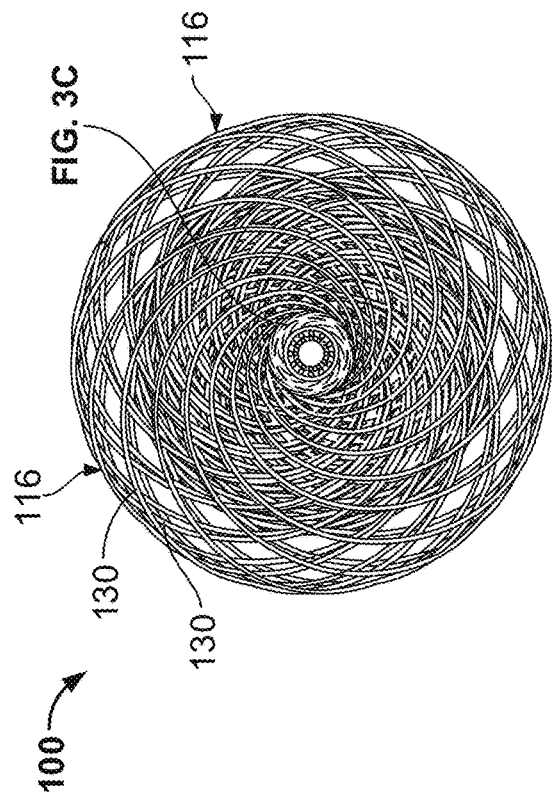
FIG. 3B
FIG. 3C

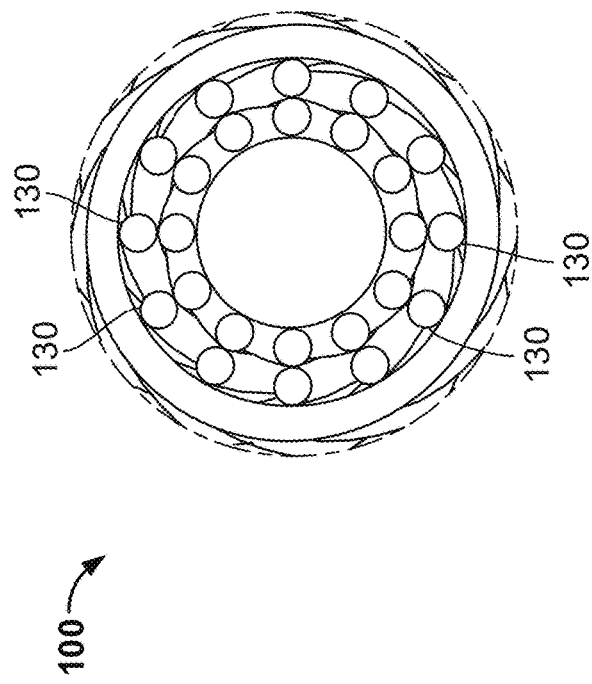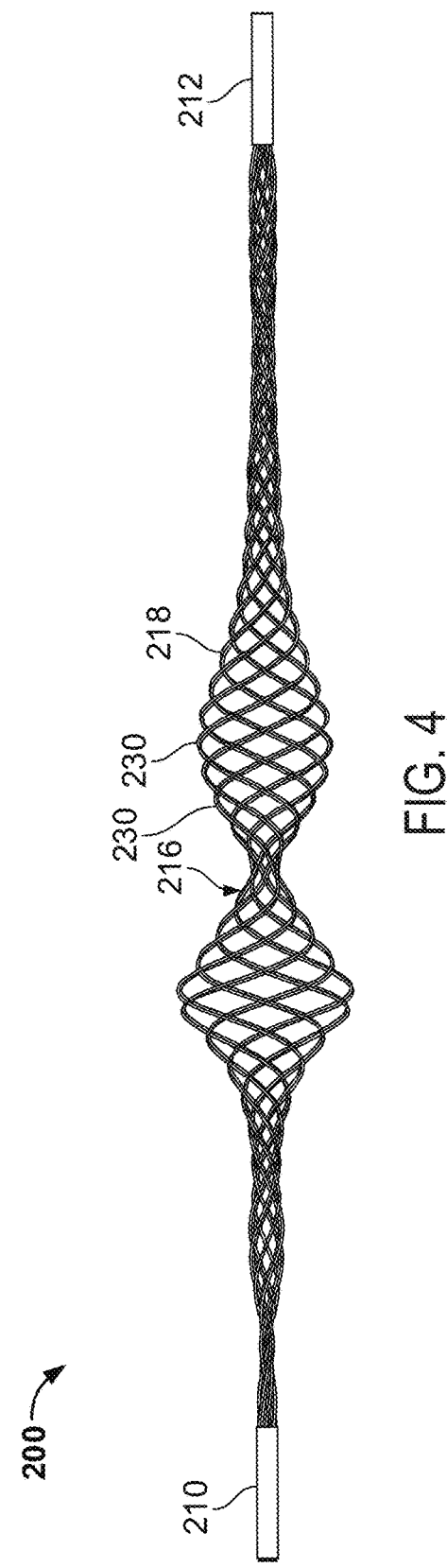

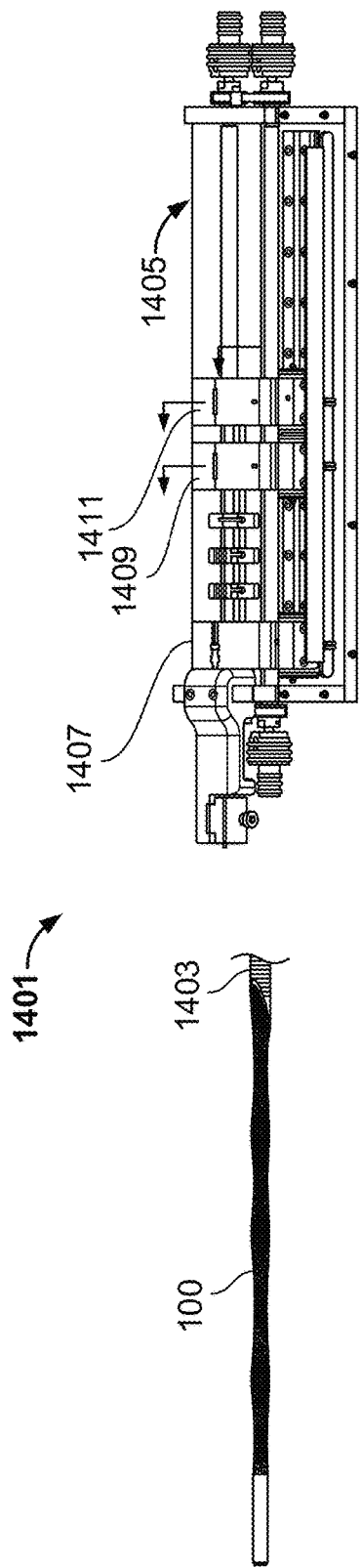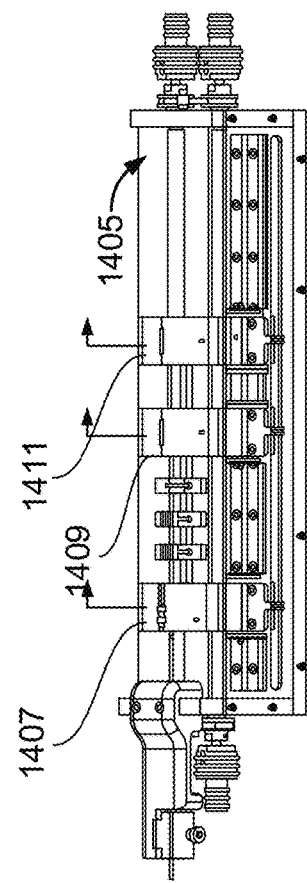
FIG. 17A
FIG. 17B

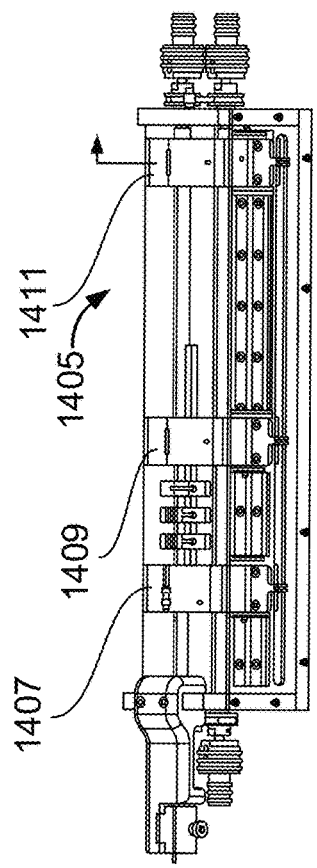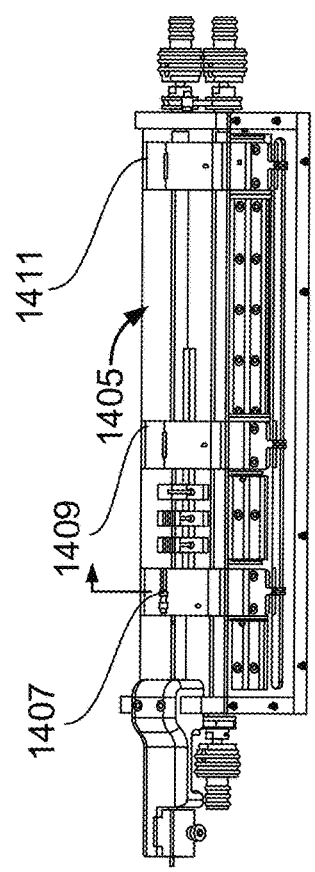
FIG. 17E
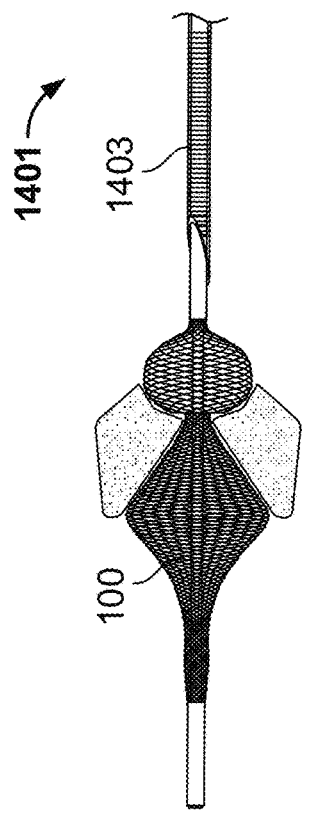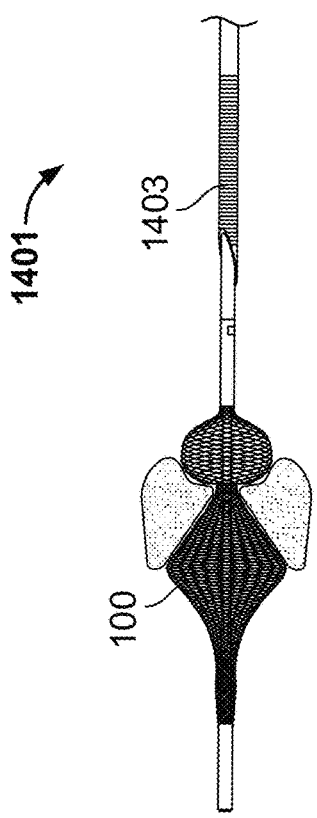
FIG. 17F

US 11,172,921 B2

HEART TISSUE ANCHORS

CROSS-REFERENCE TO RELATED APPLICATIONS

This application is a National Stage of International Application No. PCT/US2016/067275, filed Dec. 16, 2016, which claims the benefit of priority under 35 U.S.C. § 119 to U.S. Provisional Application Ser. No. 62/269,451 filed Dec. 18, 2015, the entire disclosures of which are incorporated herein by reference.

TECHNICAL FIELD

The present invention relates to heart tissue anchor devices.

BACKGROUND

A tricuspid valve is the valve located between a right atrium and a right ventricle in a mammalian heart. In a normally functioning tricuspid valve, when the valve is open, blood is allowed to be pumped from the right atrium into the right ventricle. When the valve is closed, blood is blocked from passing back from the right ventricle to the right atrium. However, when tricuspid regurgitation occurs, the tricuspid valve fails to open and close properly such that blood is allowed to flow backwards from the right ventricle to the right atrium of the heart. Tricuspid regurgitation can be treated by an annular reduction repair procedure that can be performed using a cardiac surgery procedure.

Current methods of tricuspid valve reduction surgery involves open heart surgery. The physician uses pledgets and sutures to plicate the tissue or, alternatively, uses a rigid or semi-rigid C-shaped ring to hold the valve tissue in place.

In a conventional cardiac heart valve replacement surgical procedure, the patient must typically be placed on cardio-pulmonary by-pass. During cardio-pulmonary by-pass, the flow of blood into and out of the heart and lungs is interrupted, and the blood flow is routed to a conventional blood pump and oxygenation unit. It is known that complications and side-effects are associated with cardiopulmonary by-pass, and it is generally believed that it is in the best interest of a patient to expedite the cardiac surgical procedure and remove the patent from cardio-pulmonary by-pass as quickly as possible. Complications and side effects associated with cardio-pulmonary surgery typically include the generation of emboli, hemolysis and degradation of the blood's oxygen carrying capacity, and inflammatory response in the blood. Some or all of these complications may be caused contact with the components of the cardio-pulmonary bypass equipment. The severity and incidence of potential side effects may be related to the length of the period of time that the patient is being supported on cardio-pulmonary by-pass.

Accordingly, there is a need for devices and methods for performing tricuspid regurgitation repair using minimally invasive catheter based procedures to reduce patient recovery time and health risks, as well as preserve the original tricuspid valve shape.

SUMMARY

Disclosed herein are various embodiments of heart tissue anchor devices and methods related thereto. This document provides devices and methods for delivering and attaching tissue anchors during a minimally invasive catheter based procedure, for example, a procedure for performing a heart valve reduction surgery.

In Example 1, a heart valve anchor includes a body that includes a distal portion, a distal end, a proximal portion, and a proximal end. The distal end and the proximal end define a longitudinal axis. The body includes an expandable portion including a first radially expandable portion at the distal portion of the body; a second radially expandable portion at the proximal portion of the body; and a root portion disposed between the first and second radially expandable portions. The body has a first configuration adapted to be housed at least partially within a tissue penetrating device, and a second configuration in which the first and second radially expandable portions are partially or fully expanded such that the anchor engages tissue in a region between the first and second radially expandable portions.

In Example 2, the heart valve anchor of Example 1, wherein the first and second radially expandable portions are configured to radially expand such that outer diameters at the first and second radially expandable portions are larger than an outer diameter of the root portion.

In Example 3, the heart valve anchor of Example 1 or Example 2, wherein the first and second radially expandable portions are configured to radially expand when the anchor is compressed along the longitudinal axis.

In Example 4, the heart valve anchor of any of Examples 1-3, wherein the anchor includes a shape memory material.

In Example 5, the heart valve anchor of Example 4, wherein the shape memory material includes nitinol.

In Example 6, the heart valve anchor of Example 4 or Example 5, wherein the first and second radially expandable portions of the anchor are configured to self-expand from the first configuration to the second configuration.

In Example 7, the heart valve anchor of any of Examples 1-6, wherein the first and second radially expandable portions comprise one or more spirally-wound wires.

In Example 8, the heart valve anchor of Examples 1-7, wherein the radially expandable portions includes one or more wires comprising a first wire having a first diameter, and a second wire having a second diameter, wherein the first diameter is larger than the second diameter.

In Example 9, the heart valve anchor of Example 7 or 8, further comprising first and second couplers, wherein the first coupler is disposed about and coupled to a distal end of the first radially expandable portion and the second coupler is disposed about and coupled to a proximal end of the second radially expandable portion, and wherein the first and second couplers couple the one or more wires to the distal end and proximal end, respectively.

In Example 10, the heart valve anchor of any of Examples 1-9, wherein the first and second radially expandable portions each form a peak that can be adjusted longitudinally in a distal direction or a proximal direction when the first and second radially expandable portions are compressed by an axial force.

In Example 11, the heart valve anchor of any of Examples 1-10, wherein the first and second radially expandable portions are configured to radially expand when released from the tissue penetrating device.

In Example 12, the heart valve anchor of any of Examples 1-11, wherein first and second radially expandable portions angulate to a predetermined angle relative to a longitudinal axis defined by the anchor when in the first configuration.

In Example 13, the heart valve anchor of any of Examples 1-12, wherein first and second radially expandable portions angulate about 90 degrees relative to a longitudinal axis defined by the anchor when in the first configuration.

In Example 14, an anchor assembly including an anchor of any of Examples 1-13 detachably coupled to a push rod, the anchor further comprising a means for locking the anchor in an expanded state.

In Example 15, the anchor assembly of Example 14, wherein the anchor includes a locking feature including one of expandable barbs, a hypotube clasp, an expandable stent, a collapsible pull wire, a flexible insert, and a one-directional clasp.

In Example 16, the anchor assembly of Example 14 or Example 15, further including a deployment fixture, the deployment fixture including a coupler adapted for coupling to a needle delivery device, a push rod, and an anchor assembly, the anchor assembly including the heart valve anchor of Example 1 coupled to a pull wire, the deployment fixture adapted to independently translate the needle delivery device, the push rod, and the anchor assembly in a proximal or distal direction to release the anchor.

In Example 17, a heart valve anchor includes a body that includes a distal portion, a distal end, a proximal portion, and a proximal end. The body defines a lumen therethrough and includes a radially expandable portion comprising a spirally-wound wire, and a tissue-securing means coupled to the distal portion of the body.

In Example 18, the heart valve anchor of Example 17, wherein the radially expandable portion comprises one of concave, a reverse-concave, a dual-concave, a floating, or a fixed anchor shape.

In Example 19, the heart valve anchor of Example 17 or Example 18, wherein the tissue-securing means comprises a suture coupled to the distal end of the body, and extending through the lumen and the proximal end of the body.

In Example 20, the heart valve anchor of any of Examples 17-19, wherein a distal end of the body includes a tissue piercing tip.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A shows the anchor in a collapsed, undeployed state. FIG. 2B shows the anchor in an expanded, deployed state.

FIGS. 3A-3C are a side view, a front view, and a magnified transverse cross-sectional view, respectively, of the heart valve anchor of FIGS. 2A-2C, but does not include all of the components thereof for simplicity purposes.

FIG. 4 is a side view of another exemplary heart valve anchor provided herein.

FIG. 8A is a perspective view of the heart valve anchor assembly. FIG. 8B is a side view of the inner components of the heart valve anchor assembly. FIGS. 8C-8G are side views of various embodiments of a locking feature of the anchor assembly.

FIGS. 17A-17F are illustrations of a deployment fixture and the heart valve anchor of FIGS. 2A and 2B at various states during a deployment procedure.

Figure 1B:
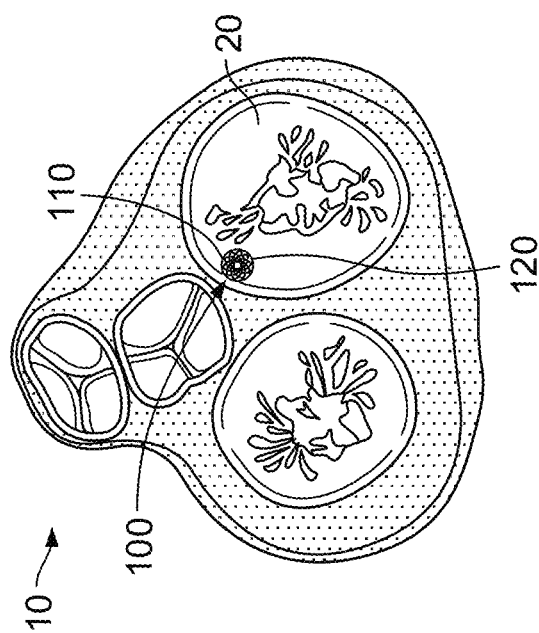
FIGS. 1A and 1B are schematic illustrations of an exemplary implanted heart valve anchor provided herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The human body has four heart valves: a pulmonary valve, a tricuspid valve, an aortic valve and a mitral valve. The purpose of the heart valves is to allow blood to flow through the heart and from the heart into the major blood vessels connected to the heart, such as the aorta and pulmonary artery.

Figure 1A:
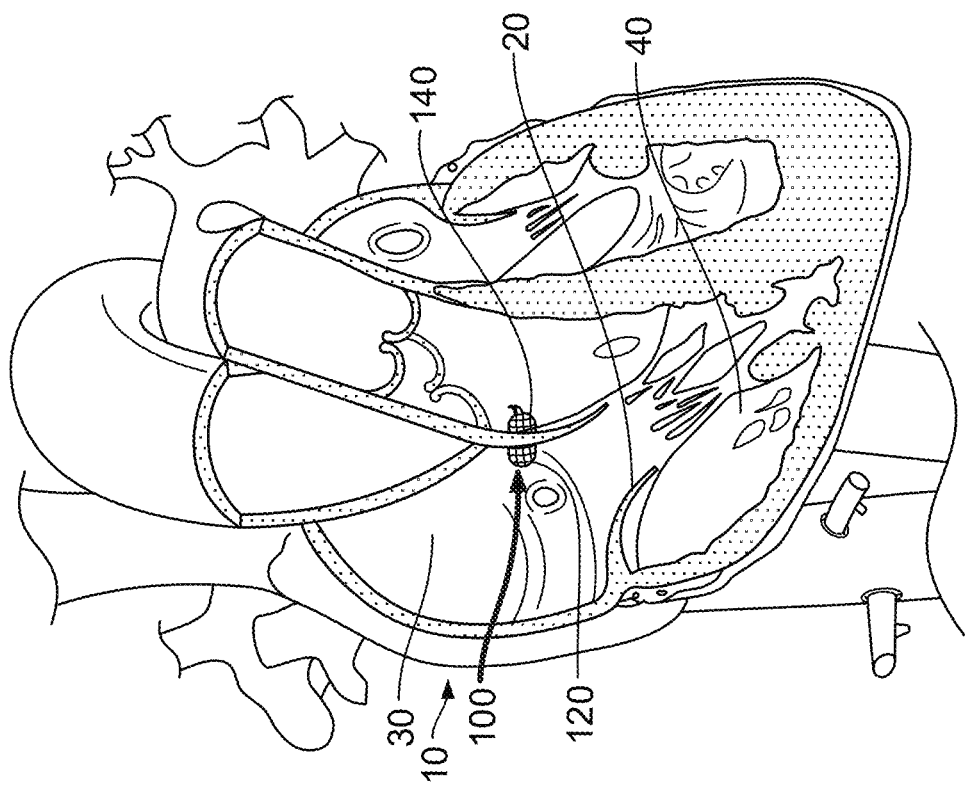
Figure 9:
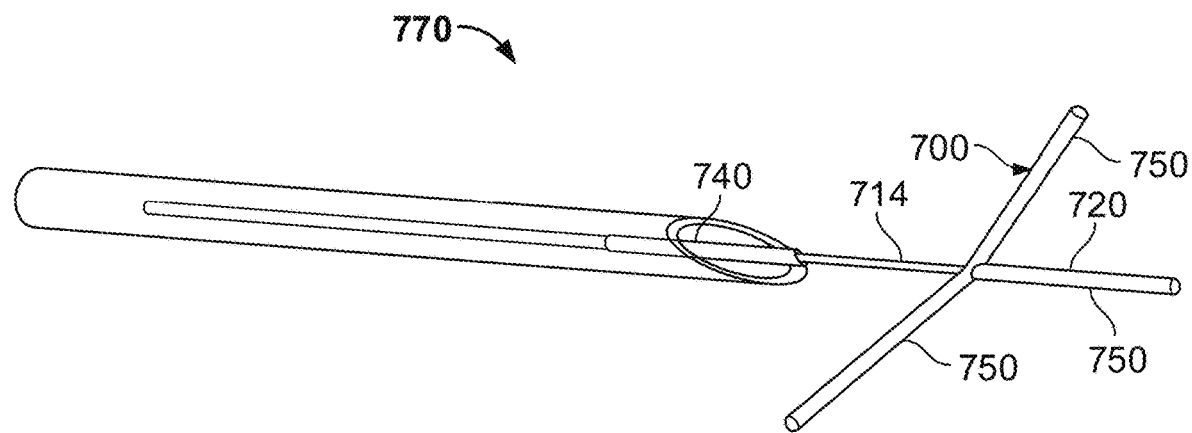
FIG. 9 is a perspective view of another exemplary heart valve anchor assembly provided herein, shown as partially deployed from a needle.

FIGS. 1A and 1B are illustrations of a heart 10 that show a tricuspid valve 20, located between the right atrium 30 and right ventricle 40, anchored with an exemplary heart valve anchor 100 provided herein. Embodiments of the heart valve anchors 100 provided herein can be delivered within a hypodermic needle (e.g., as shown in FIG. 9) of needle delivery device. The heart valve anchors 100 provided herein can be implanted into a patient by using a transcatheter tricuspid reduction system during a minimally invasive procedure method for performing a tricuspid valve reduction surgery. The anchors 100 provided herein can be used in place of pledgets and/or sutures, or in conjunction with, to perform a surgical reduction of a heart valve, e.g., the tricuspid valve.

Various embodiments of the anchors 100 provided herein include a first anchoring portion 120, a second anchoring portion 140, and a connecting portion (not shown) therebetween. The first and second anchoring portions 120, 140 are expandable portions of the anchor 100 configured to compress (anchor) together annular valve tissue to a predetermined length (which will be discussed in greater detail in later sections) when the anchor 100 is secured to tissue. The connecting portion is coupled to the first and second anchoring portions 120, 140 and maintains the predetermined anchoring length of the anchor 100 after the anchor 100 has been secured to the annular valve tissue.

Figure 2A:
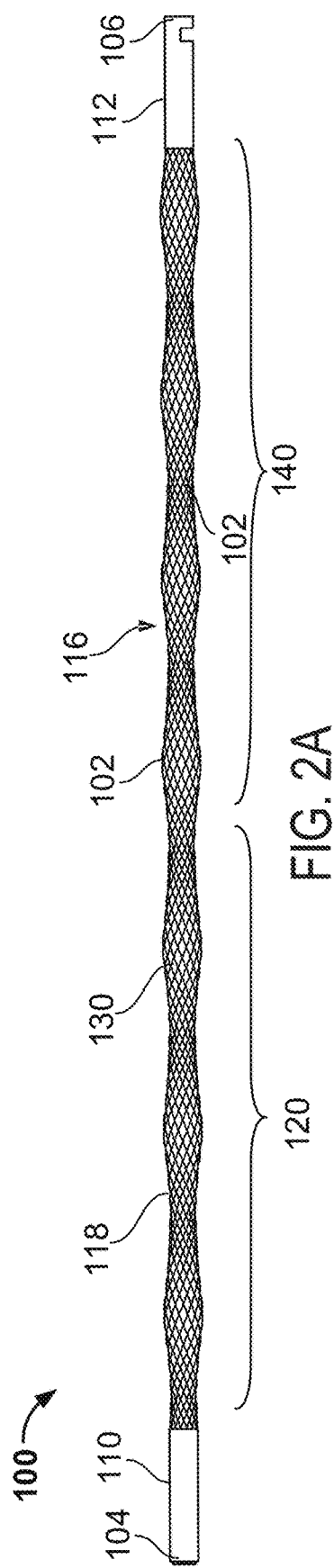
FIGS. 2A and 2B are side views of the heart valve anchor of FIG. 1 shown in two different states.
Figure 2B:
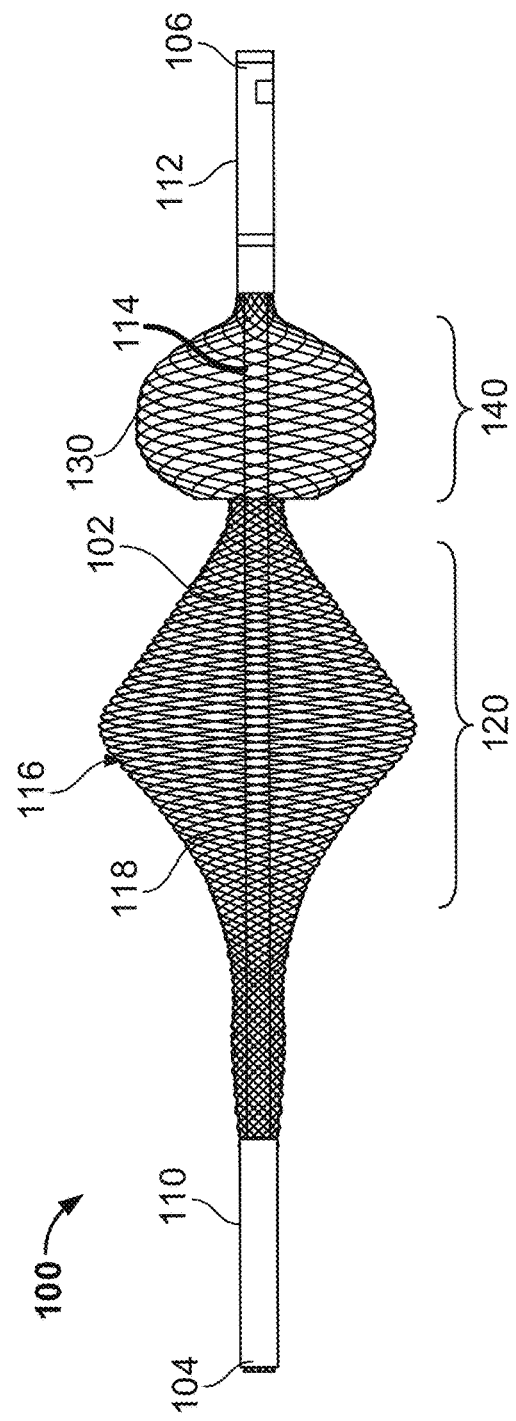

Referring to FIGS. 2A-2B, the heart valve anchor 100 of FIG. 1 has a body 102 with a distal end 104 and a proximal end 106. The anchor 100 can transition from a collapsed state (FIG. 2A) to a diametrically expanded state (FIG. 2B), respectively. The anchor 100 has a rigid body portion that includes a distal coupler 110 at the distal end 104, a proximal coupler 112 at the proximal end 106, and optionally an inner connector 114 coupled to the distal coupler. The anchor 100 also contains an expandable portion 116 disposed over the inner connector 114 and extending from the distal end 104 to the proximal end 106 of the anchor 100. The expandable portion 116 can include a (metallic) stent structure 118 formed by a plurality of wires 130 orientated in a braided configuration.

The distal and proximal couplers 110, 112 are tubular structures each disposed about the distal and proximal portions of the expandable portion 116. The couplers are configured to bind the wires 130 of the metallic stent structure 118 together such that the stent structure 118 does not become unraveled. The couplers provide a benefit of allowing a plurality of wires 130 to be coupled together (e.g., welded) at the distal and proximal ends 104, 106 of the anchor 100 while minimizing potentially damaging the wires 130. For example, in some cases, the coupler can be made of a similar material (e.g., shape memory material such as nitinol) as the wires 130.

Some embodiments of the anchors 100 provided herein can include the inner connector 114, which is coupled to the distal coupler and couplable to the proximal coupler. In the collapsed state, the inner connector 114 is locked to the distal coupler to allow the expandable portion 116 of the anchor 100 to elongate in a longitudinal direction over the inner connector 114, as desired. In the diametrically expanded state, the inner connector 114 can be locked to both the distal coupler and the proximal coupler during the procedure (as will be discussed with a tensioning method in later sections) to set a longitudinal distance between the couplers, as well as the overall anchor length. In the diametrically expanded state, the anchor 100 provided herein can maintain a fixed longitudinal length for anchoring tissue in a compressed state.

The expandable portion 116 can include a first (distal) anchoring portion (which can be referred to as a first expandable portion) 120 and a second (proximal) anchoring portion 140 (which can be referred to as a second expandable portion). The first and second anchoring portions 120, 140 are adapted to expand to capture tissue in the area between the anchoring portions. The first and second anchoring portions 120, 140 can have different, or similar, expanded shapes, when the anchor 100 is a diametrically expanded state. In particular, as depicted in FIG. 2B, the first anchoring portion 120 of the anchor 100 can expand to a substantially rhombus-shaped shape and the second anchoring portion 140 can expand to a substantially bulbous shape. In some cases, both anchoring portions can expand into a substantially rhombus-shaped shape, a substantially bulbous shape, or other shape having a larger, expanded profile.

Figure 16:
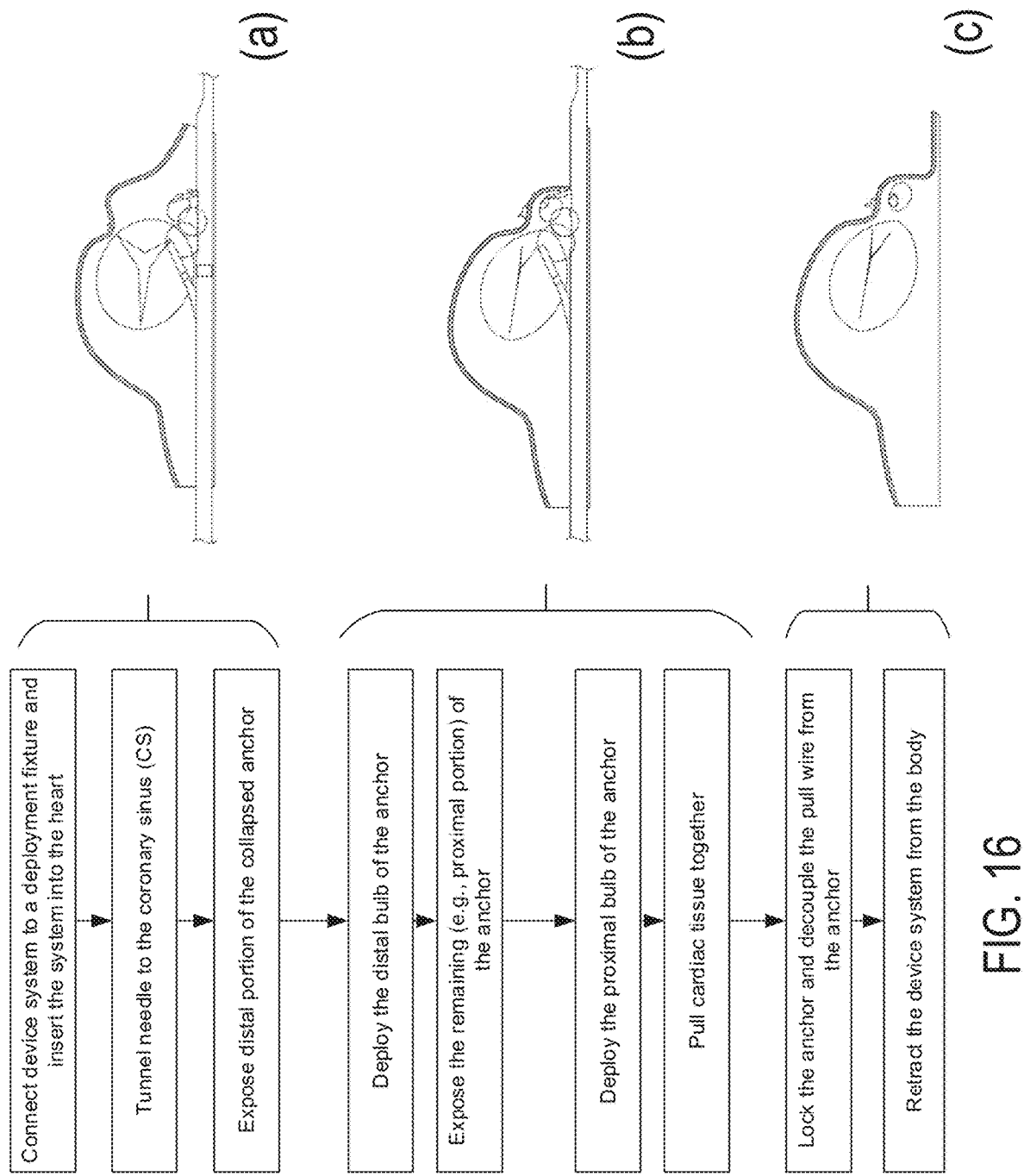
FIG. 16 is a flowchart providing steps of a method of using a heart valve tissue anchor provided herein.

The anchors 100 provided herein are adapted to be delivered within a needle lumen and deployed from a needle tip (as shown in FIG. 16). The anchors 100 are also adapted to provide a spring-like feature to reduce tissue damage that can occur to the tissue of the pulsating heart. The flexibility of the stent structure 118 reduces over-rigidity and tension that might otherwise tear or inflame tissue being anchored together by the anchors 100. In some cases, the individual wires 130 of the stent structure 118 can be spaced part from one another to create spaced regions that promote tissue ingrowth.

The anchors 100 provided herein may, in some cases, further include a fabric material (not shown) disposed over or within the stent structure 118. The fabric material can be composed of a biocompatible material, such as a polymeric material or a biomaterial, adapted to promote tissue growth. In some cases, the fabric material can include a bioabsorbable material. Suitable fabric materials can include, but are not limited to, polyethylene glycol (PEG), nylon, polytetrafluoroethylene (ePTFE)), a polyolefinic material such as a polyethylene, a polypropylene, or blends thereof, polyester, polyurethane, and combinations thereof.

The anchors 100 provided herein can be made of metals, polymers, ceramics, or combinations thereof. In some cases, the anchors 100 can include one or more biocompatible alloy materials. In some cases, the anchor 100 can include a shape memory material. Suitable materials of the anchor components can include, but are not limited to, nitinol, stainless steel, a titanium alloy, a platinum alloy, and combinations thereof. In some cases, the anchors 100 can be made of a biodegradable and/or a bioresorbable material, such as poly(L-lactide) (PLLA), polylactic acid (PLA), polyhydroxybutyrate (PHB), poly(butylene succinate), poly-ε-caprolactone, and combinations thereof.

FIGS. 3A-3C are a side view, a front view, and a transverse cross-sectional view, respectively, of the heart valve anchor 100 of FIGS. 2A and 2B, but does not show an inner connector (e.g., see inner connector 114 in FIG. 2B). The anchor 100 shown in these figures includes the distal coupler 110, the proximal coupler 112, and the expandable portion 116 extending therebetween. The depicted anchor 100 is shown in a non-stressed state, which is the state in which the anchor 100 is not subjected to any tensile or compression forces. The shape of the expandable portion 116 of the anchor 100 can be set, as desired, by heat setting anchor components (e.g., the stent structure 118), which can be made of a shape memory material (e.g., nitinol). The plurality of wires 130 that form the expandable portion 116 of the anchor 100 are coupled together by the proximal and distal couplers at the proximal and distal ends 106, 104, respectively, of the anchor 100.

Referring FIG. 3A, the anchor 100 includes the first and second anchoring portions 120, 140 configured for securing tissue. The anchor 100 includes a root portion 119, which is a reduced-diameter region between the first and second anchoring portions 120, 140. In the non-stressed state, the first anchoring portion 120 of the anchor 100 of FIG. 4A has a substantially rhombus-shaped shape and the second anchoring portion 140 has a substantially tear drop shape. Various other shapes can be contemplated for the first and second anchoring portions 120, 140 that provide a larger profile adjacent (e.g., proximally adjacent, distally adjacent, or both) to the root portion 119 to hold and compress tissue in the area between the first and second anchoring portions 120, 140. In some cases, the anchoring portions 120, 140 of the anchor can include any shape adapted for securing tissue between the anchoring portions 120, 140. In some cases, at least a portion of the anchoring portions 120, 140 of the anchor can include a flat surface for securing tissue.

In some cases, the maximum diameter "D1" (i.e., peak) of the first anchoring portion 120 can be larger than, or about equivalent to, the maximum diameter "D2" of the second anchoring portion 140 in a non-stressed state and/or a diametrically expanded state. In some cases, the maximum diameter (e.g., D1 or D2) of the first or second anchoring portion 120, 140 can increase as the length "L" of the overall anchor 100 decreases. The maximum diameter (D1 or D2) of the first or second anchoring portion 120, 140 can be dependent on the distance between peak locations of the first and second anchoring portions 120, 140, or, more specifically, the compression force being applied to the second anchoring portion 140.

The anchors 100 provided herein can be sized (e.g., diameter and length) to any suitable size. For example, in some cases, the anchor 100 can have a maximum diameter (e.g., at the first and/or second anchoring portions 120, 140) ranging from about 6.4 mm (0.25 inches) to about 25 mm (1 inch). In some cases, the maximum diameter of the anchor 100 can range from about 5 mm to about 7 mm, from about 7 mm to about 10 mm, from about 10 mm to about 12 mm, from about 12 mm to about 15 mm, from about 15 mm to about 20 mm, or from about 20 mm to about 30 mm. In some cases, the anchor 100 can have a minimum diameter (e.g., at the root portion 119, or the distal or proximal couplers 110, 112) ranging from about 2.5 mm (0.1 inches) to about 13 mm (0.5 inches), e.g., from about 2.5 mm to about 4 mm, from about 4 mm to about 6 mm, from about 6 mm to about 8 mm, from about 8 mm to about 10 mm, or from about 10 mm to about 13 mm.

In some cases, the anchor 100 can have a non-compressed length ranging from about 25 mm (1 inch) to about 76 mm (3 inches), e.g. from about 25 mm to about 30 mm, from about 30 mm to about 50 mm, from about 50 mm to about 76 mm. In some cases, the compressed length of the anchor can range from about 12.7 mm (0.5 inches) to about 51 mm (2 inches), e.g., from about 12.7 mm to about 15 mm, from about 15 mm to about 20 mm, from about 20 mm to about 30 mm, from about 30 mm to about 40 mm, or from about 40 mm to about 51 mm. In some cases, the different in length between the compressed and non-compressed anchor can range from about 6.4 mm (0.25 inches) to about 64 mm (2.5 inches), e.g., from about 6.4 mm to about 10 mm, from about 10 mm to about 20 mm, from about 20 mm to about 30 mm, from about 30 mm to about 40 mm, from 40 mm to about 50 mm, or from about 50 mm to about 64 mm.

Referring to FIG. 4, another exemplary heart valve anchor 200 provided herein that includes a different stent structure as compared to the anchor 100 of FIGS. 3A-3C. The anchor 200 provided herein includes a distal coupler 210, a proximal coupler 212, and an expandable portion 216. The expandable portion 216 of the depicted anchor 200 includes a stent structure 218 including a plurality of wires 230. As compared to the previous anchor 100, the depicted anchor 200 includes a fewer number of wires 230 as compared to the number of wires 130 of anchor 100 of FIGS. 3A-3C. In some cases, the stent structure 218 of the anchor 200 can include about 10 wires to about 50 wires (e.g., about 10 wires, about 12 wires, about 14 wires, about 16 wires, about 18 wires, about 20 wires, about 24 wires, about 26 wires, about 30 wires, about 40 wires, about 50 wires). The number of wires of the stent structure 218 can be selected to obtain a desired flexibility and tensile strength in the anchor 200. Increasing the number of wires increases the likelihood of obtaining an adequate welding bond between the wires 230 of the expandable portion 216 and the couplers.

The wires 230 of the stent structure 218 can be sized to any suitable dimension that provides the anchor 200 with the desired flexibility, structural integrity, and a stent configuration suitable for tissue growth. A suitable wire diameter range can span from about 0.0127 millimeters (mm) (0.0005 inches) to about 0.127 mm (0.005 inches) (e.g., from about 0.0127 mm (0.0005 inches) to about 0.0254 mm (0.001 inches), from about 0.0254 mm (0.001 inches) to about 0.0508 mm (0.002 inches), from about 0.0508 mm (0.002 inches) to about 0.0762 mm (0.003 inches), from about 0.0762 mm (0.003 inches) to about 0.102 mm (0.004 inches), or from about 0.102 mm (0.004 inches) to about 0.127 mm (0.005 inches)). In some cases, a smaller sized wire diameter (e.g., 0.0127 mm (0.0005 inches) to about 0.0508 mm (0.002 inches)) can have greater flexibility and aid in facilitating tissue growth within the expandable portion 216 of the anchor 200 by allowing a greater number of wires 230 to be used in constructing the anchor 200. In some cases, a larger sized wire diameter (e.g., 0.0762 mm (0.003 inches) to about 0.127 mm (0.005 inches)) can provide an anchor 200 with increased tensile strength.

Figure 5A:
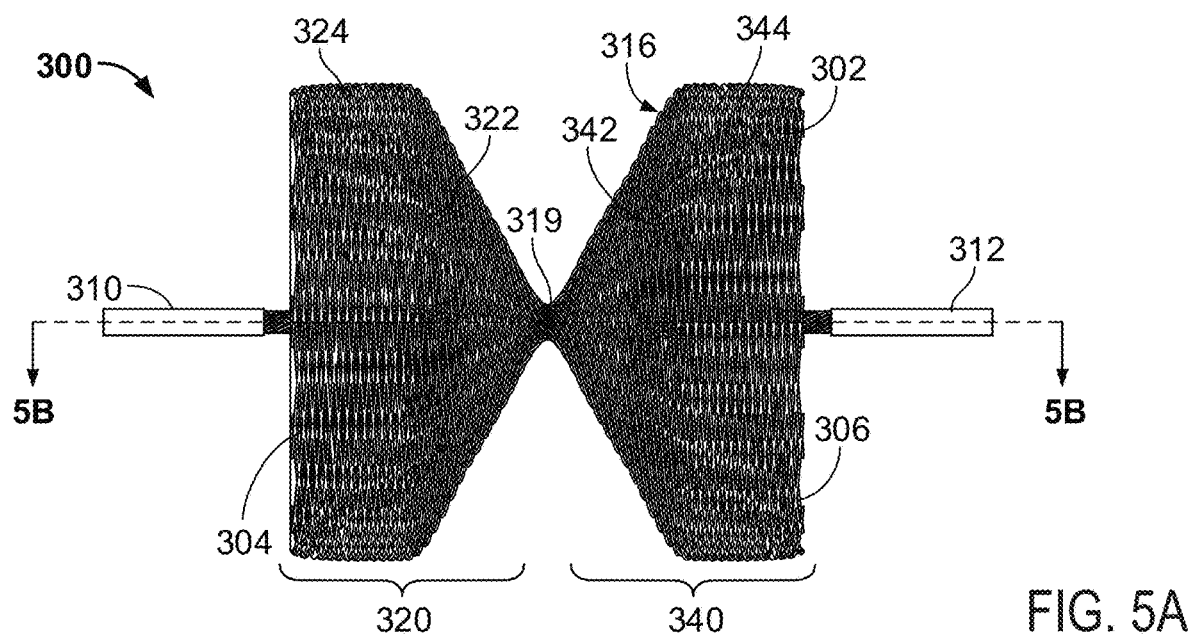
FIGS. 5A and 5B are a side view and a cross-sectional side view of the anchor.
Figure 5B:
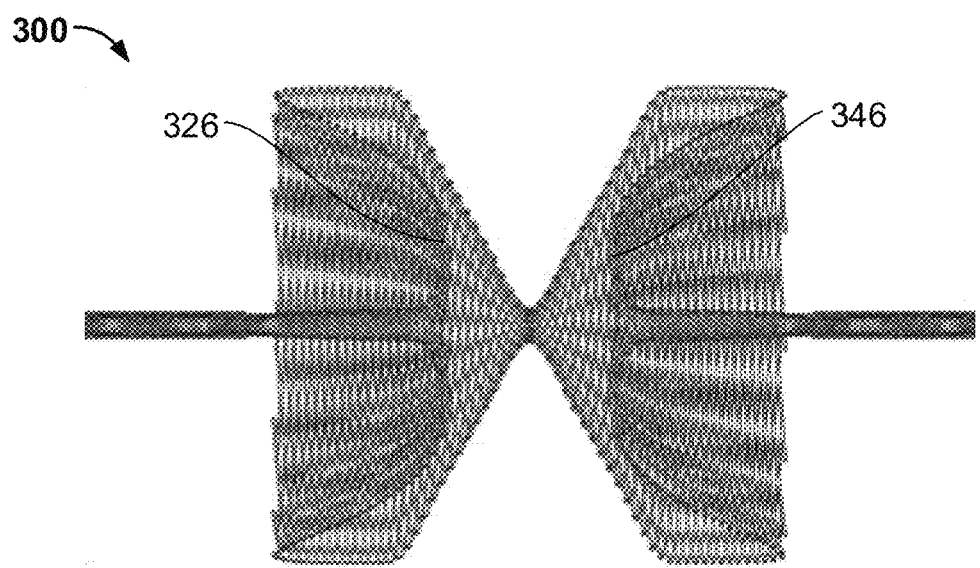

Referring to FIGS. 5A and 5B, another exemplary heart valve anchor 300 provided herein includes a body 302 with a distal end 304 and a proximal end 306. FIGS. 5A and 5B provide a side view and a cross-sectional side view of the anchor 300. The anchor 300 includes a distal coupler 310, a proximal coupler 312, and an expandable portion 316. Certain components, such as the distal and proximal couplers 310, 312, are similar to the corresponding components 110, 112, 114 discussed with the anchor 100 of FIGS. 3A-3C, thus the focus of the discussion of the present embodiment will be focused on the expandable portion 316 of the anchor 300. The anchor 300 can include an inner connector (not shown; see 114 of FIG. 2B) extending from the distal end 304 to the proximal end 306 and within an annular cavity formed by the expandable portion 316.

The expandable portion 316 of the anchor 300 includes first and second anchoring portions 320, 340 and a v-shaped root portion 319 therebetween. Each anchoring portion has a concave design that includes an outer profile having a frustoconical portion 322, 342 and a cylindrical portion 324, 344. Each anchoring portion has one end that folds in on itself to create a concave region 326, 346 that forms a depressed feature that faces away from tissue when the anchor 300 is implanted. The first anchoring portion 320 includes a distal concave region 326 that faces the distal coupler 310. The second anchoring portion 340 includes a proximal concave region 346 that faces the proximal coupler 312. The concave regions 326, 346 of anchor 300 help to maintain tissue contact between the first and second anchoring portions 320, 340 of the anchor 300 while the heart pulsates, and its overlapping fold increases the area for potential cell growth on the expandable portion 316.

Figure 6A:
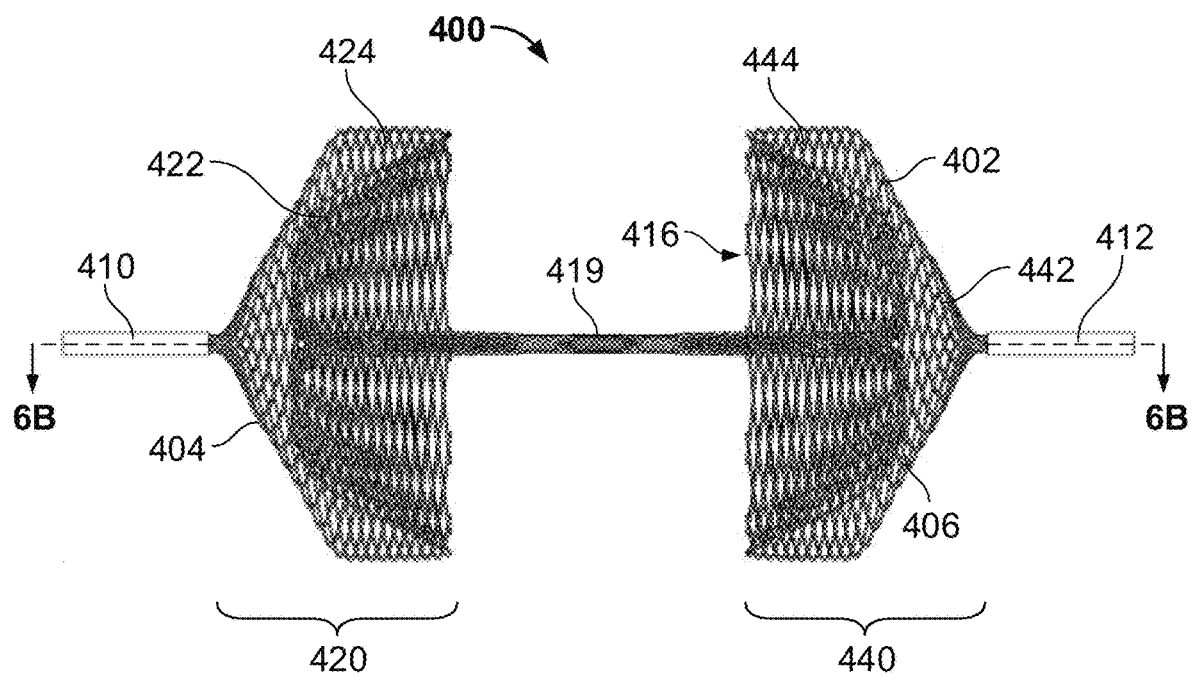
FIGS. 6A and 6B are a side view and a cross-sectional side view of the anchor.
Figure 6B:
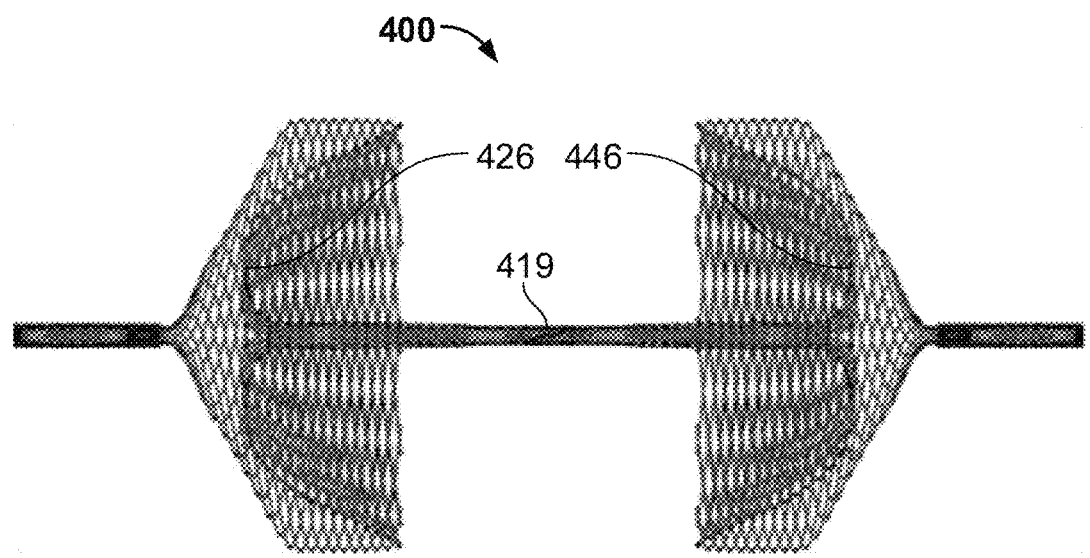

Referring to FIGS. 6A-6B, another exemplary heart valve anchor 400 provided herein includes a body 402 with a distal end 404 and a proximal end 406. FIGS. 6A and 6B, and 6C provide a side view and a cross-sectional side view of the anchor 400. The anchor 400 includes a distal coupler 410, a proximal coupler 412, and an expandable portion 416. Certain components, such as the distal and proximal couplers are similar to the components of the anchor 100 of FIGS. 3A-3C, thus the focus of the discussion of the present embodiment will be focused on the expandable portion 416 of the anchor 400. In some cases, the anchor 400 optionally includes an inner member disposed within an annular cavity formed by the expandable portion 416.

The expandable portion 416 of the anchor 400 includes first and second anchoring portions 420, 440 and a root portion 419 between. Each anchoring portion includes an outer profile with a frustoconical portion 422, 442 and a cylindrical portion 424, 444. Each anchoring portion has a one end that folds in on itself to create a reverse-concave region 426, 446 with a depressed feature that faces toward tissue when the anchor 400 is implanted. The first anchoring portion 420 includes a distal reverse-concave region 426 that faces the second anchoring portion 440. The second anchoring portion 440 includes a proximal reverse-concave region 446 that faces the first anchoring portion 420. The root portion 419 includes a portion of the expandable portion 416 disposed about the inner connector (not shown; see, e.g., 114 of FIG. 2B). As such, the root portion 419 is substantially cylindrical in shape and has a diameter that ranges from about 0.508 mm (0.020 inches) to about 1.02 mm (0.040 inches). The reverse-concave regions 426, 446 of anchor 400 help to maintain tissue contact between the first and second anchoring portions 420, 440 of the anchor 400 while the heart pulsates, and its overlapping fold increases the area for potential cell growth on the expandable portion 416. The anchor 400 can include an inner connector (not shown; see inner connector 114 of FIG. 2B) disposed within an annular cavity formed by the expandable portion 516, wherein the inner connector facilitates locking of the expandable portion 516 when the anchor is implanted in the patient's body.

Figure 7A:
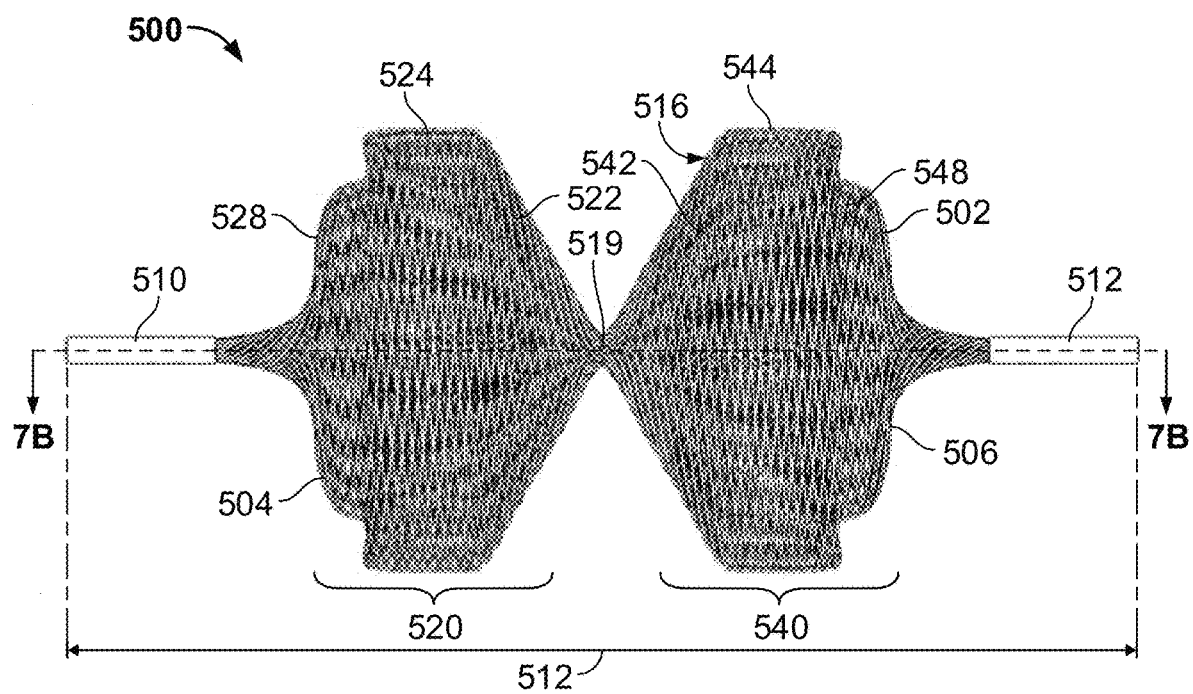
FIGS. 7A and 7B are a side view and a cross-sectional side view of the anchor.
Figure 7B:
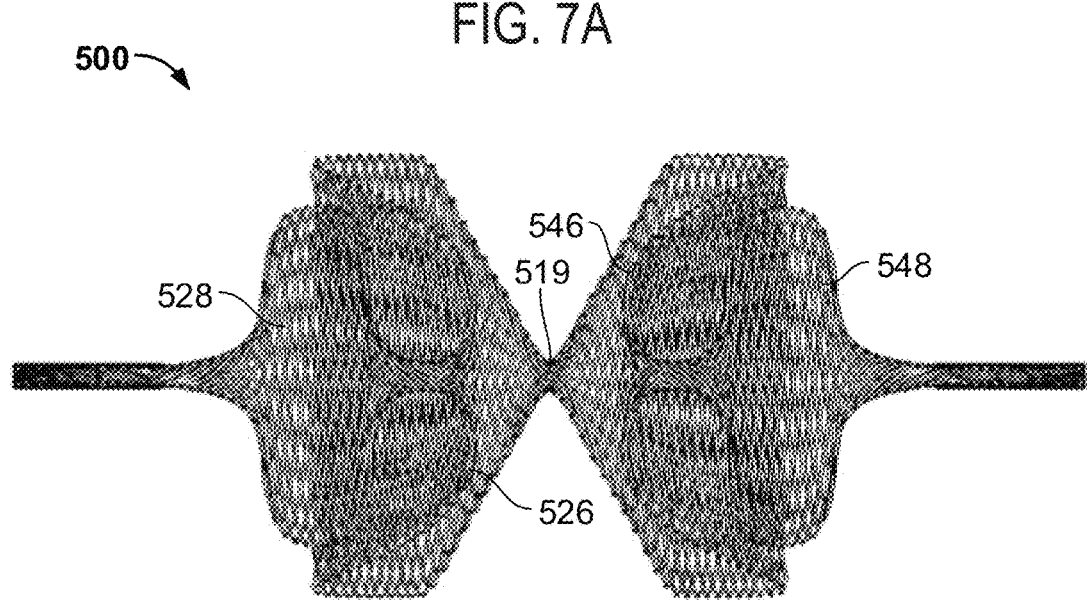

Referring to FIGS. 7A and 7B, another exemplary heart valve anchor 500 provided herein includes a body 502 with a distal end 504 and a proximal end 506. FIGS. 5A and 5B provide a side view and a cross-sectional side view of the anchor 500. The anchor 500 includes a distal coupler 510, a proximal coupler 512, and an expandable portion 516. Certain components, such as the distal and proximal couplers are similar to the components of the anchor 100 of FIGS. 3A-3C, thus the focus of the discussion of the present embodiment will focus on the expandable portion 516 of the anchor 500. In various embodiments, the anchor 500 can locked by a locking mechanism, which will be discussed with FIGS. 8C-8G, in later sections. In certain cases, the anchor 500 can include an inner connector (e.g., inner connector 114 of FIG. 2B) disposed within an annular cavity formed by the expandable portion 516, wherein the inner connector facilitates locking of the expandable portion 516 when anchored in the patient's body.

The expandable portion 516 of the anchor 500 includes first and second anchoring portions 520, 540 and a v-shaped root portion 519 therebetween. Each anchoring portion has an outer profile with a frustoconical portion 522, 542, a cylindrical portion 524, 544, and bulbous portion 528, 548. Each anchoring portion has one end that folds in on itself to create a concave region 526, 546 between the cylindrical and the bulbous portions 528, 548. For example, the first anchoring portion 520 can include a distal concave region that faces the distal coupler. The second anchoring portion 540 can include a proximal concave region that faces the proximal coupler. The concave regions 526, 546 and bulbous portions 528, 548 of anchor 500 increase the area for potential cell growth on the expandable portion 516 of the anchor 500.

Figure 8A:
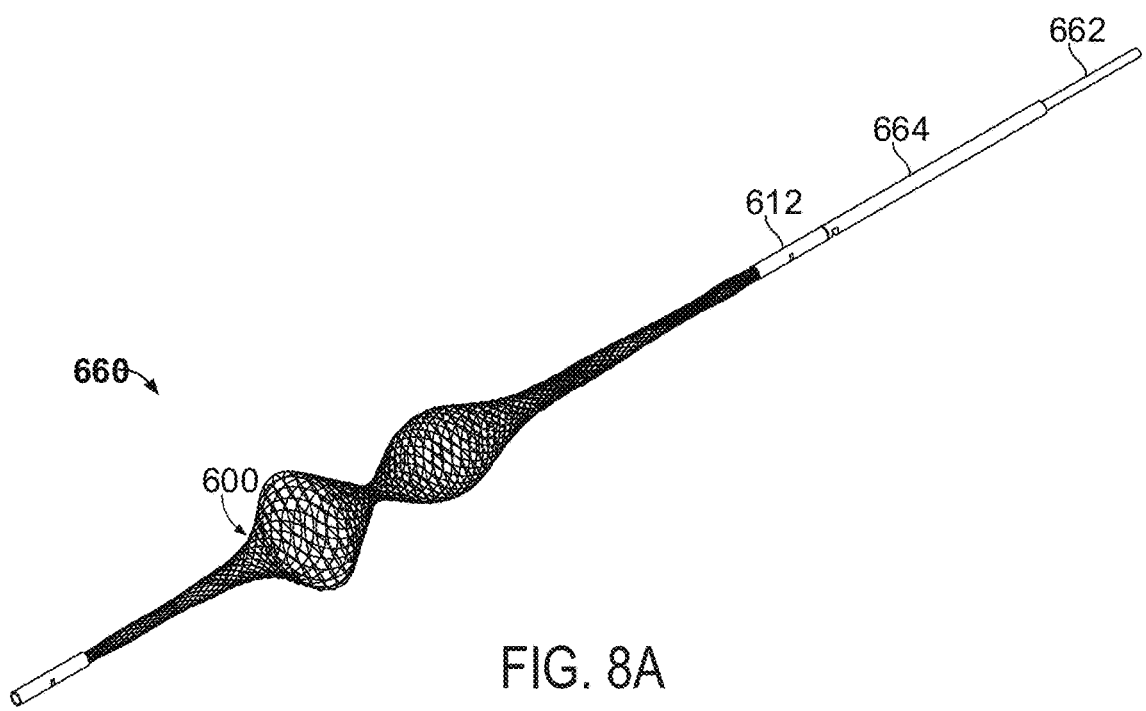
FIGS. 8A-8G are a perspective view and side views, respectively, of a distal portion of an exemplary heart valve anchor assembly provided herein.

FIG. 8A is a perspective view of a distal portion of an exemplary heart valve anchor assembly 660 provided herein that includes a heart valve anchor 600, a detachable pull rod 662 (or hypotube), and a push rod 664. The push rod 664 can include a tubular body that has a distal end and a proximal end, the body defining a lumen configured to receive the pull rod. The push rod can be slidably disposed over the inner rod. The push rod can be sized such that distal end of the push rod mates with the proximal end 606 of the anchor 600, in particular, the proximal coupler 612. The push rod can be adapted to apply compressional force to the anchor 600 during the deployment of the anchor 600 when used in conjunction with the inner connector.

Figure 8B:
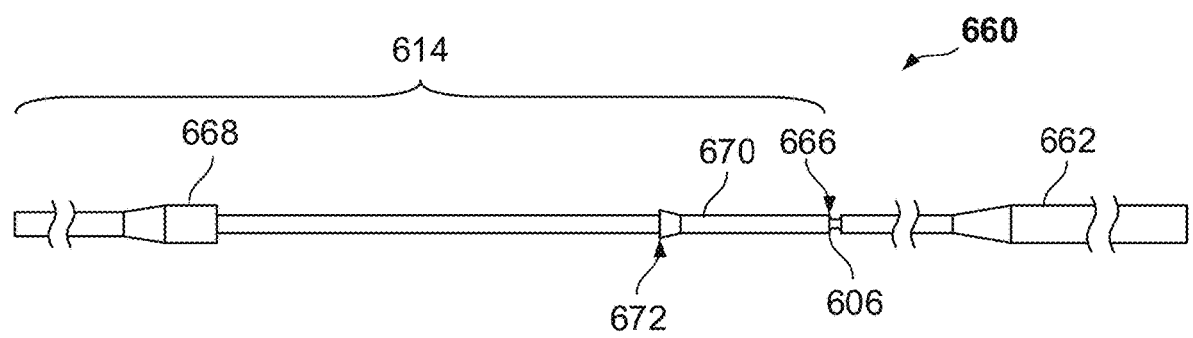
Figure 8C:
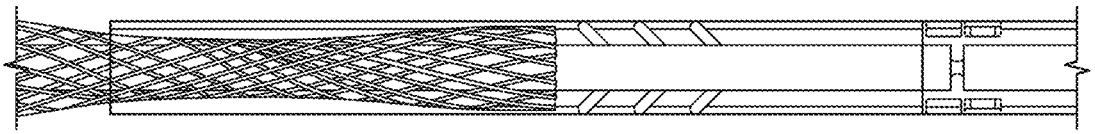
Figure 8D:
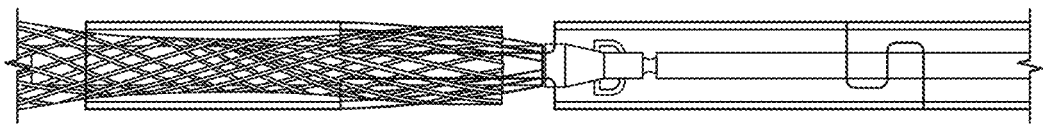
Figure 8E:
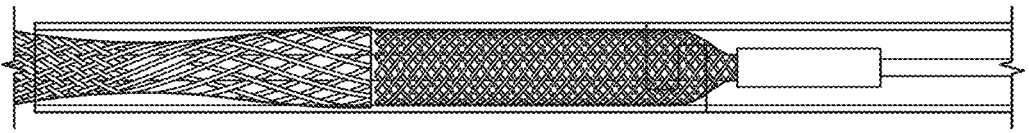
Figure 8F:
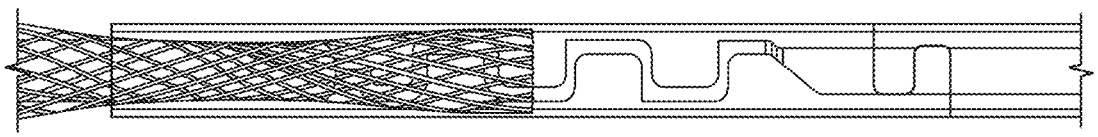
Figure 8G:
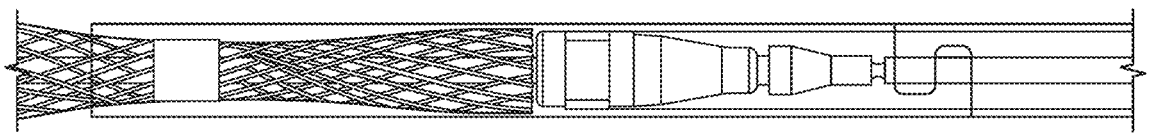

FIG. 8B shows an optional inner component, e.g., the inner connector 614, which can be disposed within the anchor 600 provided herein, and coupled to the pull rod 662. The inner connector 614 include a distal portion 668, a proximal portion 670, and a locking portion 672 configured to lock the anchor 600 in a diametrically expanded state when the locking portion 672 is positioned proximal to the proximal coupler. The conical shape of the locking portion 672 allows the locking portion 672 to slide within a lumen of the proximal coupler, but its barbed end prevents the locking portion 672 from reinserting into a proximal coupler (e.g., the proximal coupler of FIG. 8A) once pulled from a lumen of the proximal coupler. The pull rod 662 can be used in conjunction with the push rod 664 to longitudinally compress the anchor 600 during anchor deployment. For example, the pull rod 662 may be pulled in a proximal direction while the position of the push rod is either maintained or advanced in a distal (opposite) direction to expand the anchor 600. In some cases, the anchor 600 and the detachable inner rod are one integral component. In some cases, the anchor 600 and the inner rod are bonded together by a bonding process, such as soldering, adhesive bonding, or laser welding.

The inner connector 614 may be detachably coupled to the pull rod 662 of the heart valve anchor assembly 660. In particular, a proximal portion 670 of the inner connector 614 of the anchor 600 provided herein can be decoupled from the pull rod 662 in a necked region 666 of the anchor 600. In some cases, the anchor assembly 606 can be configured to release inner connector 614 of the anchor 600 from the pull rod 662 when a threshold tensile force is applied to the anchor assembly 606. As shown in FIG. 8B, the anchor assembly 606 can include the necked region 666 proximate to the proximal portion 670 of the anchor 600. The anchor 600 can be decoupled from the pull rod 662 in the necked region 666 when the anchor assembly 660 is subjected to a threshold tensile force. In some cases, the threshold tensile force is about 8.9 Newtons (N), 2 pounds force (lbf). In some cases, the threshold tensile force can range from about 4.5 N (1 lbf) to 22 N (5 lbf) (e.g., from about 4.5 N (1 lbf) to about 8.9 N (2 lbf), from about 8.9 N (2 lbf) to about 13 N (3 lbf), from about 13 N (3 lbf) to about 18 N (4 lbf), or from about 18 N (4 lbf) to about 22 N (5 lbf)).

Certain embodiments of the anchor assembly 606 can include other means for decoupling the inner connector 614 of the anchor 600 from the pull rod 662. For example, in some cases, the anchor assembly 606 can include mating threaded portions on the proximal portion 670 of the inner connector 614 and the distal end of the pull rod 662. The threaded portions can be adapted to decouple the inner connector 614 from the pull rod 662 when the pull rod 662 is rotated (e.g., clockwise) relative to the inner connector 614. In some cases, the anchor assembly 606 includes a heating element configured to decouple the inner connector 614 of the anchor 600 from the pull rod 662 by application of heat, generated by an electrical, thermal, or radio-frequency source, that melts at least a portion of the anchor assembly 606. In some cases, the inner connector 614 and the pull rod 662 have mating components (e.g., a socket and mating ball) configured to release when subjected to a threshold axial load.

FIGS. 8C-8G provide various embodiments of alternative locking features of the anchor assembly that connects the proximal end of the anchor to a push wire. The locking features shown in FIGS. 8C-8G can be optionally applied to an inner connector that extends from the distal end to the proximal end of an anchor, as shown in FIG. 8B. Alternatively, the locking features can be included in an inner portion (a proximal inner portion, or a distal inner portion).

In some cases, the locking feature can include expandable barbs (FIG. 8C), a hypotube clasp (FIG. 8D), an expandable stent (FIG. 8E), a collapsible pull wire (FIG. 8F), a flexible insert (FIG. 8G), or a one-directional clasp (e.g., locking portion 672 of FIG. 8B), configured to lock the expandable portion at the proximal coupler. For example, the expandable barbs, which are in a collapsed state when within a lumen of the proximal coupler, expand in a radially outward direction when the locking feature of the inner portion, or the inner connector, is pulled out of the proximal coupler lumen.

FIG. 9 is a perspective view of another exemplary heart valve anchor assembly 770 provided herein, shown with an anchor 700 partially deployed from a needle. The depicted anchor 700 can include a first (distal) anchoring element 720, a proximal anchoring element 740, and a connector element 714 therebetween.

The distal and proximal anchoring elements can each include two, three, or more than three collapsible prongs 750 (e.g., two, three, four, five, ten, twenty, thirty, fifty, a hundred, or more than a hundred prongs). Each prong has a first end coupled to the connector element and a free second end. In some cases, each prong is configured to align with a longitudinal axis defined by the connector element such that the anchor 700 can be inserted into a tissue-penetrating device, such as a needle lumen. In a diametrically expanded configuration, each prong can angulate a predetermined angle relative to the connector element. Each prong 750 can be biased toward angulation by the application of various methods, such as shape-setting a shape memory material into a desired angled configuration, or incorporating a spring, or a spring-like component (e.g., elastic polymer tubing) into the prong 750. In some cases, each prong can angulate about 90 degrees relative to the connector element when the anchor 700 is in a diametrically expanded configuration. In some cases, each prong can angulate from about 10 degrees to 145 degrees (e.g., from about 10 degrees to about 30 degrees, from about 30 degrees to about 60 degrees, from about 60 degrees to about 90 degrees, from about 90 degrees to about 145 degrees).

Figure 10:
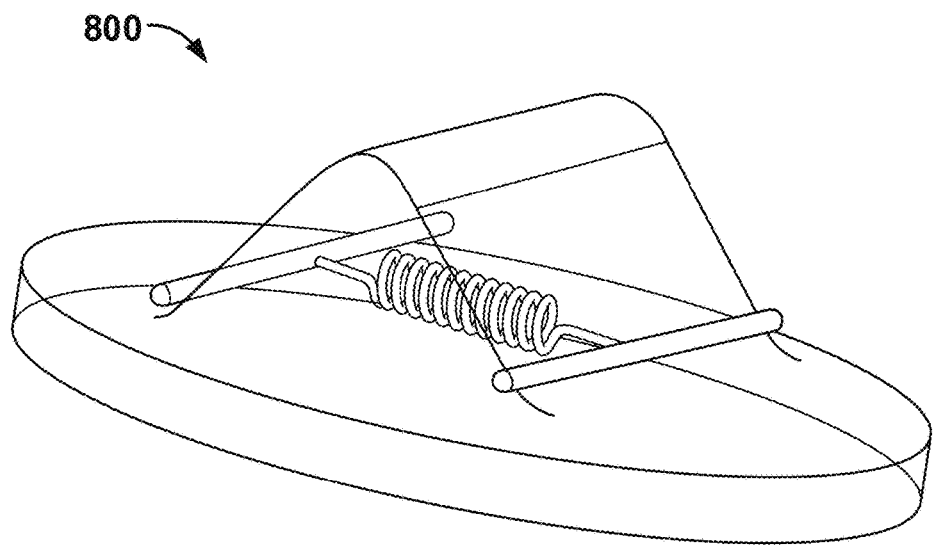
FIG. 10 is a perspective view of another exemplary heart valve anchor provided herein, shown in a fully deployed state.

FIG. 10 is a perspective view of another exemplary heart valve anchor 800 provided herein, shown in a fully deployed state. The depicted anchor 800 can have a body that includes a distal anchoring element, a proximal anchoring element, and a connector element therebetween. In some cases, the distal and proximal anchoring elements can include a nitinol rod. In some cases, the connector element can include a spring.

The distal and proximal anchoring element each include one collapsible T-bar prong. Similar to the anchor 700 of FIG. 9, the center point of each prong is coupled to the connector element. In a collapsed configuration, each prong can be aligned with a longitudinal axis defined by the connector element such that the anchor body can be inserted into a tissue-penetrating device, such as a needle lumen. In a diametrically expanded configuration, each prong can articulate to a predetermined angle relative to the connector element.

The connector element can be configured to provide an elastic connection between the distal and proximal anchoring elements. For example, in some cases, the connector element includes a coiled spring or an elastic polymer segment. The connector element can have a varying length that is dependent on axial forces being applied to the connector element. For example, when the connector element is subjected to a tensile force or compression force, the connector element can expand or reduce a length of the overall anchor from about 1% to about 100% (e.g., from about 1% to about 5%, from about 5% to about 10%, from about 10% to about 20%, from about 20% to about 30%, from about 30% to about 50%, or from about 50% to about 100%). In some cases, the connector element can elongate the anchor about 1%, about 2%, about 3%, about 4%, about 5%, about 10%, about 20%, about 30%, about 40%, about 50%, about 60%, about 70%, about 80%, about 90%, about 100%, or more than 100% relative to the anchor original (non-stressed) length.

Figure 15:
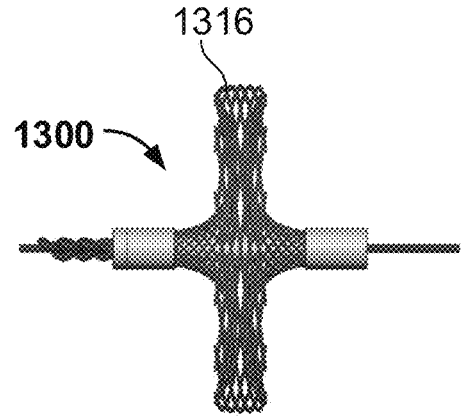

FIGS. 11-15 are side views of various exemplary heart valve anchors 900, 1000, 1100, 1200, 1300 provided herein. As shown, each of the various heart valve anchors can include a single expandable portion that can anchor against a targeted tissue surface. In some cases, the single expandable portion is a radially expandable portion that includes one of concave (FIG. 11), a reverse-concave (FIG. 12), a dual-concave (FIG. 13), a floating (FIG. 14), or a fixed anchor shape (FIG. 15). The heart valve anchor can be anchored in place, in some embodiments, against the tissue surface by fixing the anchor in place, for example, by suturing the anchor to the tissue or using a coupler (e.g., clip) to hold the anchor in position. Accordingly, various embodiments of the anchors provided herein include suture attachable anchors that can be used in open heart surgery, or minimally invasive heart surgery.

Figure 11:
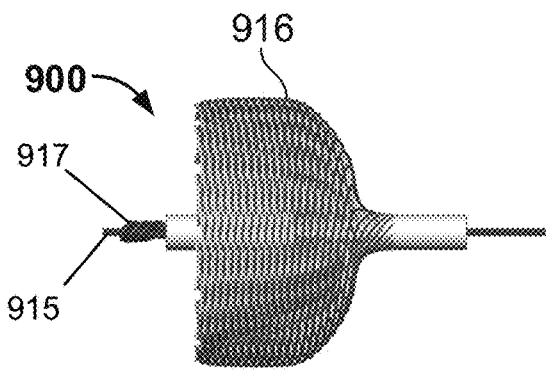
FIGS. 11-15 are side views of exemplary heart valve anchors provided herein.
Figure 12:
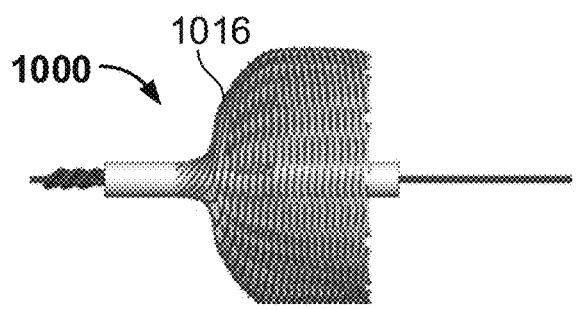
Figure 13:
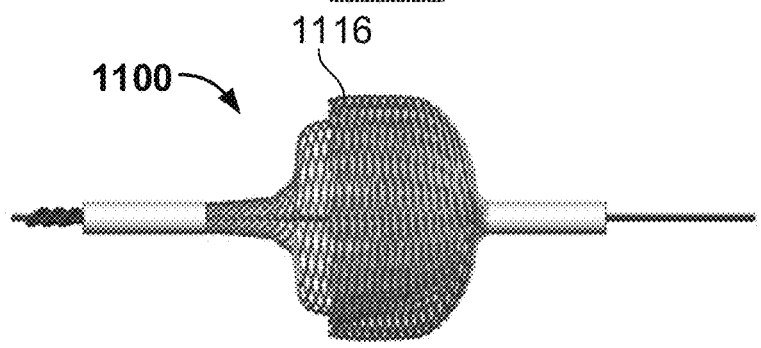
Figure 14:
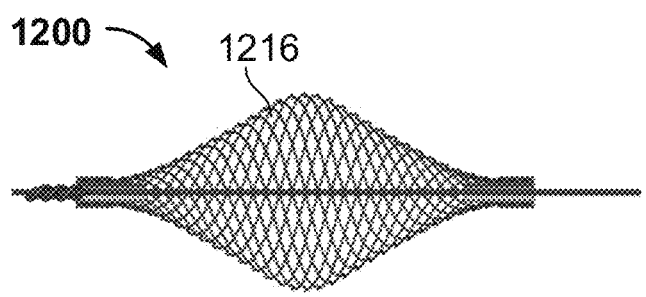

Referring to FIG. 11, a heart valve anchor 900 provided herein that includes a body having a distal portion, a distal end, a proximal portion, and a proximal end. The body can define a lumen therethrough, extending from the distal end to the proximal end. The body can include a radially expandable portion at the distal portion of the body. As shown, the anchor of FIG. 11 include a single concave expandable portion 916. In some cases, the body defines a lumen therethrough and includes a radially expandable portion comprising a spirally-wound wire, and a tissue-securing means 917 coupled to the distal portion of the body.

A suture or wire can be coupled to the distal end of the body, and extended through the lumen and the proximal end of the body. The suture or wire may be extended from the proximal end of the anchor body and anchored to tissue to hold the tissue anchor in position. The anchor pulling the anchor against the tissue and tying a knot in the suture to secure the anchor tightly against the tissue. In some cases, the knot in the suture can be pushed into place with a knot pushing element (e.g., rod).

The distal end of the body can optionally include a tissue piercing tip 915. The tissue piercing tip 915 may be made from a portion of the suture or wire coupled to the distal end of the body that extends distally therefrom. The tissue piercing tip 915 can allow the anchor to partially or fully penetrate tissue during anchor deployment. In one example, when a needle catheter device has already penetrated tissue, the anchor may be advanced out of the needle catheter device and further penetrate the tissue until it has emerged from a tissue surface. In another example, the anchor with a tissue piercing tip 915 may be used to penetrate tissue fully by piercing a tissue surface and penetrating through the entire tissue area.

The anchor may optionally include a locking feature described herein at the proximal portion of the body. The anchor may optionally include a locking feature including one of expandable barbs, a hypotube clasp, an expandable stent, a collapsible pull wire, a flexible insert, and a one-directional clasp.

Referring to FIGS. 12-15, the expandable portion of the heart valve anchors 1000, 1100, 1200, 1300 provided herein can include one of various shapes. For example, the anchor of FIG. 12 has a reverse-concave expandable portion 1016 that includes a depressed feature adapted to face towards tissue. The anchor of FIG. 13 has dual-concave design 1116 that includes an expanded bulb portion insides of a depressed feature configured to face away from tissue. The anchor of FIG. 14 has a floating expandable portion 1016.

The floating expandable portion 1016 can form a peak (maximum diameter) at its center when the anchor is not subjected to any axial forces, however, the peak of the floating expandable portion 1016 may form distal or proximal to the center when an axial force is exerted on the expandable portion. The anchor of FIG. 15 includes a single-fixed expandable portion 1116. The single-fixed expandable portion 1316 includes a disk-shaped expandable portion 1316, in which a first set of inner wires is fixed to a second set of outer wires. The single-fixed expandable portion 1316 has a flat transverse region that can be shaped in one of various cross-sectional shapes (e.g., circular, square, rectangular) to provide a pledget surface during a heart valve surgical procedure.

FIG. 16 is a flowchart providing a series of steps along with illustrations demonstrating a method of using a heart valve tissue anchor provided herein. The steps of use can include delivering and attaching tissue anchors during a minimally invasive catheter based procedure, for example, a procedure for performing a heart valve reduction surgery.

The illustrations of FIG. 16, labeled (a)-(c), show an images of a tricuspid regurgitation device system extending from the superior vena cave to the inferior vena cave within a patient's heart. The system includes an introducer, a visualization catheter, and a tissue penetrating and anchoring (TPA) device. Certain components of the system (e.g., introducer) are inserted into the jugular vein using an over-the-wire method following a JAG and snare wire introduction into the anatomy. The introducer allows other components of the system, such as the visualization catheter, to be introduced and fed into the heart through the jugular vein. The visualization catheter can be advanced to the right atrium from the superior vena cava and positioned in the right atrium. The visualization catheter can include a visualization balloon in which saline is inputted into the balloon through an exterior port attached at a proximal end of the visualization catheter. A visualization catheter can be steerable such that the visualization balloon can be positioned within the atrium to establish visualization of the coronary sinus (CS).

Once the introducer has been positioned within the heart, a hypodermic needle device, pre-loaded with anchors provided herein and connected to a deployment fixture (discussed in greater detail with FIGS. 17A-17F), can be fed through the opening in a femoral vein. The needle device can be advanced through the inferior vena cava over a guide wire until the needle device reaches the entrance of the heart's right atrium. While the balloon of the visualization catheter is deployed at the coronary sinus location, the needle device can be advanced from the introducer through the coronary sinus at a 70 degree angle by using an actuator (e.g., a hand-operated or automated micrometer or dial).

Referring to illustration (a), the needle device can be tunneled through the tricuspid annular tissue, and around the posterior leaflet of the tricuspid valve while a camera within visualization balloon is steered to follow the needle and guide the physician. The needle can be advanced until a distal end of the needle exits the edge of the posterior leaflet. The needle device can be slowly retracted until the needle tip exits the edge of the posterior leaflet. A stylet at the proximal end of the anchor can be advanced to push against the anchor to expose deploy a distal portion of the first anchor head from the needle tip.

Referring to illustration (b), the needle can continue to be retracted back through the tunneled tissue so the needle is fully retracted from the tissue and the remaining (proximal) portion of the anchor is exposed. The proximal portion of the anchor can be deployed and diametrically expanded such that the tunneled tissue is disposed between the distal and proximal portions of the anchor. The anchor can be compressed, squeezing the tissue between the anchors, and locked into place. The needle device can be retracted completely back into the catheter; leaving the anchor behind in the heart valve tissue.

Referring to illustration (c), the locked anchor can be applied to placate the annular tissue of the posterior leaflet and reduce the tricuspid valve. The delivery device system components can be removed from the patient's body once the anchor has been locked into place. The needle device can be removed from the body through the femoral vein, and the catheter and introducer can be removed from the body through the jugular vein.

FIGS. 17A-17F provide a series of illustrations of a system 1401 showing the various stages of the anchor 100 of FIG. 1 being deployed from a needle device 1403 and locked into a final state. In particular, the illustrations show the distal portion of the system 1403 (which includes a distal portion of the needle device and the anchor), and a corresponding proximal portion of the system 1403 (which includes a deployment fixture 1405 coupled at the proximal end of the needle device 1403).

Referring to FIG. 17A, the distal portion of the system 1401 shown includes a needle device 1403 that contains within its lumen a collapsed anchor 100. The proximal portion of the system is a deployment fixture (handle) 1405 that includes a multi-component coupler, and three (block) actuators slidably disposed along one or more drive shafts. The multi-component coupler includes a first coupler configured to couple to a needle shaft of the needle device, a second coupler configured to couple to a push rod, and a third coupler configured to couple to a pull wire. The three actuators include a first actuator 1407 adapted for translating distally or proximally the needle device, a second actuator 1409 for translating distally or proximally the push rod, and a third actuator 1411 for translating distally or proximally the pull wire. As shown in FIG. 17A, once the system components have been attached to the deployment fixture 1405, all three actuators 1407, 1409, 1411 may be distally translated (as depicted by the arrows) to advance the needle device and the components contained therein (e.g., anchor, pull wire, and push rod) into targeted tissue. The needle device 1403 may be optionally disposed within a sheath during delivery through an introducer and unsheathed before advanced into tissue.

A distal portion of the anchor 100 can be exposed from the distal tip of the needle device 1403 once the needle has fully tunneled through the targeted tissue. The distal portion of the anchor 100 can be exposed such that the proximal portion of the anchor 100 remains collapsed in the needle lumen. The anchor 100 can be exposed by distally translating the second and third actuators 1409, 1411 of the deployment fixture 1405 at about equal rates and distances.

The distal portion of the anchor 100 can be diametrically expanded by translating the pull wire proximally, while leaving the push rod stationary. The pull wire can be proximally translated by sliding the third actuator 1411 in a proximal direction.

Referring to FIG. 17B, the system 1401 can be proximally translated to compress the tissue abutting the proximal surface of the distal portion of the anchor 100 by proximally translating all three actuators 1407, 1409, 1411 in a proximal direction. In this step, the tissue is compressed by the distal portion of the anchor 100 to reduce the size of the posterior leaflet.

Figure 17C:
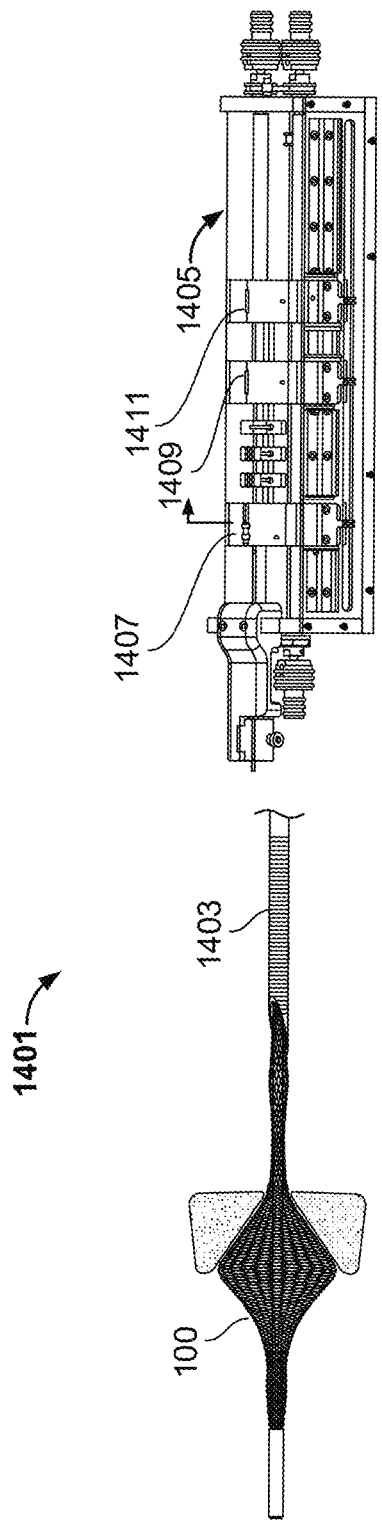

Referring to FIG. 17C, the needle 1403 can be retracted to expose the proximal portion of the anchor 100. In this step, the first actuator 1407 is proximally translated to retract the needle 1403, while the second and third actuators 1409, 1411 are held in place.

Figure 17D:
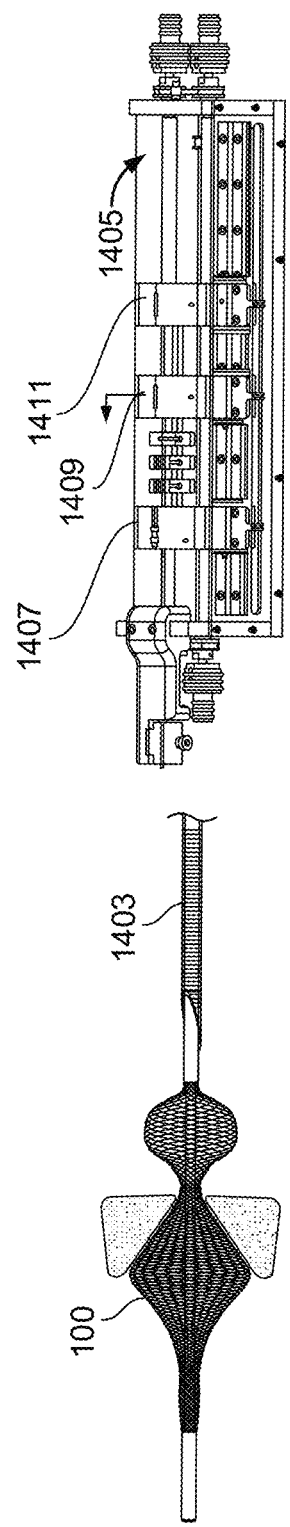

Referring to FIG. 17D, the proximal portion of the anchor 100 is diametrically expanded to secure the tissue between the distal and proximal portions of the anchor 100. The proximal portion of the anchor 100 can be diametrically expanded by distally translating the push rod, thus, applying compressional force on the anchor 100. The push rod can be distally translated by slidably moving the second actuator 1409 in a proximal direction while holding the first and third actuators 1407, 1411 stationary.

Referring to FIG. 17E, the anchor 100 is locked into its final position by releasing the anchor 100 from the pull wire. In some cases, the anchor 100 can be released retracting the pull wire with a predetermined tensile force. For example, the pull wire may be detached from the anchor 100 if a tensile force of about 8.9 N (2 lbf) or greater is applied to the anchor assembly (which includes the pull wire and anchor). To apply a tensile force on the anchor assembly the third actuator 1411 can be proximally translated while holding the first and second actuators 1407, 1409 stationary in the deployment fixture 1405.

Referring to FIG. 17F, the anchor 100 can be released from the system (e.g., the needle and push rod) 1401 such that the system 1401 can be removed from the patient's body. In some cases, the push rod includes a c-shaped clasp connector that couples the push rod to the anchor 100 during a device delivery procedure. The clasp connector can be disconnected by retracting the needle and exposing the clasp connector distal to the needle tip. Needle retraction is accomplished by proximally translating the first actuator 1407 while holding the second and third actuators stationary 1409, 1411. Since the pull wire has been detached from the anchor, the clasp connector automatically unlatches from the anchor, once exposed from the needle lumen, releasing the anchor 100 in the tissue. The system 1401 can be withdrawn from the patient's body, as desired.

It should be understood that one or more design features of the devices provided herein can be combined with other features of other devices provided herein. In effect, hybrid designs that combine various features from two or more of the device designs provided herein can be created, and are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein. All references, publications, and patents referred to herein, including the figures and drawings included therewith, are incorporated by reference in their entirety.

We claim:

1. A heart valve anchor comprising:
a body that includes a distal portion, a distal end, a proximal portion, and a proximal end, the body defining a lumen therethrough and comprising:
a radially expandable portion comprising a spirally-wound wire;
a distal coupler directly attached to a distal end of the radially expandable portion;
a tissue piercing tip directly connected to the distal coupler; and
a tissue-securing means coupled to the distal portion of the body;
wherein the tissue piercing tip is formed from a portion of the tissue-securing means.

2. The heart valve anchor of claim 1, wherein the radially expandable portion is configured to radially expand when the anchor is compressed along the longitudinal axis.

3. The heart valve anchor of claim 1, wherein the anchor comprises a shape memory material.

4. The heart valve anchor of claim 3, wherein the shape memory material comprises nitinol.

5. The heart valve anchor of claim 3, wherein the radially expandable portion is configured to self-expand.

6. The heart valve anchor of claim 1, wherein the radially expandable portion forms a peak that can be adjusted longitudinally in a distal direction or a proximal direction when the radially expandable portion is compressed by an axial force.

7. The heart valve anchor of claim 1, wherein the anchor further comprises a means for locking the anchor in an expanded state.

8. The heart valve anchor of claim 7, wherein the means for locking comprises one of expandable barbs, a hypotube clasp, an expandable stent, a collapsible pull wire, a flexible insert, and a one-directional clasp.

9. The heart valve anchor of claim 1, wherein the radially expandable portion comprises one of concave, a reverse-concave, a dual-concave, a floating, or a fixed anchor shape.

10. The heart valve anchor of claim 1, wherein the tissue-securing means comprises a suture coupled to the distal end of the body, and extending through the lumen and the proximal end of the body.

* * * * *